US012741029B2

(12) United States Patent
Jang

(10) Patent No.: US 12,741,029 B2
(45) Date of Patent: Sep. 22, 2026

(54) COMPOSITION FOR PREVENTING, AMELIORATING, OR TREATING GASTRITIS OR PEPTIC ULCER COMPRISING ANTHOCYANIN-NEGATIVELY CHARGED POLYSACCHARIDE COMPLEX AS ACTIVE INGREDIENT

(71) Applicant: JBKLAB CO., LTD., Gyeonggi-do (KR)

(72) Inventor: Bong Keun Jang, Gyeonggi-do (KR)

(73) Assignee: JBKLAB CO., LTD., Seongnam-si (KR)

( * ) Notice: Subject to any disclaimer, the term of this patent is extended or adjusted under 35 U.S.C. 154(b) by 1145 days.

(21) Appl. No.: 17/621,956

(22) PCT Filed: Jun. 26, 2020

(86) PCT No.: PCT/KR2020/008343

§ 371 (c)(1),
(2) Date: Dec. 22, 2021

(87) PCT Pub. No.: WO2020/263010

PCT Pub. Date: Dec. 30, 2020

(65) Prior Publication Data

US 2022/0249675 A1 Aug. 11, 2022

(30) Foreign Application Priority Data

Jun. 27, 2019 (KR) ........................ 10-2019-0077417

(51) Int. Cl.

*A61K 47/55* (2017.01)
*A23L 33/00* (2016.01)
*A23L 33/10* (2016.01)
*A61K 31/352* (2006.01)
*A61K 47/61* (2017.01)
*A61P 1/04* (2006.01)

(52) U.S. Cl.

CPC .............. *A61K 47/55* (2017.08); *A23L 33/10* (2016.08); *A23L 33/40* (2016.08); *A61K 31/352* (2013.01); *A61K 47/61* (2017.08); *A61P 1/04* (2018.01); *A23V 2002/00* (2013.01)

(58) Field of Classification Search

CPC .. A61K 31/352; A61V 2250/2104; A61P 1/04
See application file for complete search history.

(56) References Cited

U.S. PATENT DOCUMENTS 8,367,126 B2 2/2013 Mumper et al.

FOREIGN PATENT DOCUMENTS

KR 10-2009-0007146 A 1/2009
KR 10-2012-0126587 A 11/2012
KR 10-2015-0010671 A 1/2015
KR 10-2018-0009627 A 1/2018
KR 10-2018-0123042 A 11/2018
KR 10-2019-0047626 A 5/2019
WO 2016/048059 A1 3/2016

OTHER PUBLICATIONS

Li, Alcohol 42 (2008) 683-687. (Year: 2008).*
Valle, J., "Disappearance of Gastritis after Eradication of *Helicobacter pylori*: A Morphometric Study. A morphometric study," Scandinavian Journal of Gastroenterology, vol. 26, No. 10, Oct. 1991, pp. 1057-1065.
Collen M. J et at., "Gastric ulcers differ from duodenal ulcers evaluation of basal acid output," Digestive Diseases and Sciences, vol. 38, Dec. 1993, pp. 2281-2286.
International Search Report and Written Opinion received for PCT Patent Application No. PCT/KR20/008343, mailed on Oct. 13, 2020, 13 pages (4 pages of English Translation and 9 pages of Original Document).
Kim, Jwa Jin, "Effects of Sweet Potato Fractions on Alcoholic Hangover and Gastric Ulcer," Master's thesis, Graduate School of Chungbuk National University, Aug. 2008, pp. 37.
Shusong W. et al., "The Discussion on the application of anthocyanidins in animal feed", 2011, vol. 32, No. 21, pp. 48-51. (English abstract available).
Bae et al., "Optimized preparation of anthocyanin-rich extract from black rice and its effects on in vitro digestibility," Food Sci Biotechnol, Aug. 2017, 26(5):1415-1422.
King et al., "Composition, polyphenol bioavailability, and health benefits of aronia berry: a review," Journal of Food Bioactives, International Society for Nutraceuticals and Functional Foods, Sep. 2020, 11: 13-20.
Mattioli et al., "Anthocyanins: A Comprehensive Review of Their Chemical Properties and Health Effects on Cardiovascular and Neurodegenerative Diseases," Molecules, Aug. 2020, 25: 3809.
Meng et al., "Composition and antioxidant activity of anthocyanins from *Aronia melanocarpa* cultivated in Haicheng, Liaoning, China," Food Bioscience, May 2019, 30: 100413.

* cited by examiner

*Primary Examiner* — Layla D Berry
(74) *Attorney, Agent, or Firm* — LEYDIG, VOIT & MAYER, LTD.

(57) ABSTRACT

The present invention relates to a composition for preventing, ameliorating, or treating gastritis or peptic ulcer, comprising an anthocyanin-negatively charged polysaccharide complex as an active ingredient and, more specifically, to a composition for preventing, ameliorating, or treating gastritis or peptic ulcer, comprising an anthocyanin-negatively charged polysaccharide complex as an active ingredient, the composition exhibiting a synergistic effect as compared to anthocyanins or each of negatively charged polysaccharides. The composition comprising an anthocyanin-negatively charged polysaccharide complex as an active ingredient provided by the present invention exhibits a significantly excellent effect of relieving lesions of gastritis or peptic ulcer, and thus can be very effectively used in the development of a composition for preventing, ameliorating, or treating gastritis or peptic ulcer.

5 Claims, 3 Drawing Sheets

Analysis : Kruskal-Wallis test:
Kruskal-Wallis statistic: 17.60
p=0.0035

Analysis : One-way ANOVA
Post-Hoc: Tukey's test $F(3,32)=10.484$

**; $P<0.01$

***; $P<0.001$

COMPOSITION FOR PREVENTING, AMELIORATING, OR TREATING GASTRITIS OR PEPTIC ULCER COMPRISING ANTHOCYANIN-NEGATIVELY CHARGED POLYSACCHARIDE COMPLEX AS ACTIVE INGREDIENT

CROSS REFERENCE TO RELATED APPLICATIONS

This patent application is a nationalization of and claims priority to PCT Application No. PCT/KR2020/008343 filed on Jun. 26, 2020 entitled "COMPOSITION FOR PREVENTING, AMELIORATING, OR TREATING GASTRITIS OR PEPTIC ULCER COMPRISING ANTHOCYANIN-NEGATIVELY CHARGED POLYSACCHARIDE COMPLEX AS ACTIVE INGREDIENT," which claims priority to Korean Patent Application 10-2019-0077417, filed Jun. 27, 2019. Each of the aforementioned applications are incorporated by reference herein in their entirety.

BACKGROUND OF THE INVENTION

1. Field of the Invention

The present invention relates to a pharmaceutical composition for preventing, ameliorating, or treating gastritis or peptic ulcer, comprising an anthocyanin-negatively charged polysaccharide complex as an active ingredient and, more specifically, to a pharmaceutical composition for preventing, ameliorating, or treating gastritis or peptic ulcer, comprising an anthocyanin-negatively charged polysaccharide complex exhibiting a synergistic effect as compared to anthocyanin or each of negatively charged polysaccharides as an active ingredient.

2. Description of the Related Art

Koreans have many digestive diseases such as gastritis and peptic ulcer due to their eating habits. These diseases have a high recurrence rate after initial treatment. Peptic ulcer is a disease in which a circular, oval, or linear ulcer occurs in a part of the mucous membrane of the digestive tract. This disease frequently occurs in the areas where gastric juice with strong digestive power comes into contact, that is, the lower esophagus, the gastric vestibule, the proximal portion of the duodenum, the Meckel diverticulum, and the gastric sutures. Since this disease most often occurs in the stomach and duodenum, both gastric and duodenal ulcers are generally called peptic ulcer. Pathologically, when ulcers exist in the mucous membrane of the stomach and intestines, it is called erosion or acute superficial ulcer. When the superficial ulcer reaches the muscularis mucosa, passes through the submucosa and reaches the muscularis, it is called ulcer. When the ulcer becomes severe, the damaged area reaches the serosa and gastric juice leaks into the abdominal cavity, causing severe pain and even requiring surgical operation. Although peptic ulcer can heal spontaneously without clinical symptoms, most ulcer patients complain of discomfort such as heartburn or sour belching. Peptic ulcer is caused by the breakdown of homeostasis due to hyperactivity of an offence factor or weakening of a defense factor (Shay et al., In Gastroenterology, (Buchus, H. L & Sanunders, W. B. Co.): 420, 1963). The offence factor includes hydrochloric acid (HCl) secreted from parietal cells of the gastric glands and pepsin, a digestive enzyme, secreted from chief cells. In particular, hydrochloric acid is recognized as the main offence factor. Recently, infection with a bacterium called Helicobacter pylori has been pointed out as an important cause among the offence factors (Scan J. Gastroenterol., 26(suppl):6, 1991). It is also well known that continuous alcohol consumption causes gastritis and peptic ulcer. On the other hand, the defense factor includes the mucosal layer, mucin surrounding the surface of the digestive tract mucosa, blood flow in the mucous membrane, and prostaglandin (PG), a component constituting the mucous membrane.

Treatment methods for gastritis and gastric ulcer include antacids that neutralize excess gastric juice, anticholinergics that reduce acid secretion, histamine antagonists that inhibit gastric acid release, and gastric mucosal protective agents that increase the resistance of the gastric lining to digestive juices and aid in recovery. Recently, there is a drug therapy that prescribes a combination of the above drugs and antibiotics to remove Helicobacter pylori.

However, when these drugs are used, the recurrence rate is high, and there is a problem that it must be taken for a long time. In fact, it has been reported that ulcer is cured when the above drugs are taken for about 6 weeks, but most of the patients recur after about 1 year. In addition, there are reports that ranitidine, cimetidine, and famotidine can cause gastric tumors when taken for a long time for the treatment of gastric ulcer, and reports that long-term use of omeprazole causes neuroendocrine cell tumors. Therefore, there is an urgent need to develop a therapeutic agent for gastritis and gastric ulcer that is safe for the human body.

SUMMARY OF THE INVENTION

Accordingly, the present inventors repeated intensive research to develop a natural product-based therapeutic agent for gastritis and peptic ulcer. As a result, the present inventors have found that the anthocyanin-negatively charged polysaccharide complex exhibits significantly improved preventive or therapeutic effect on peptic ulcer compared to that of each substance, and completed the present invention.

It is an object of the present invention to provide a pharmaceutical composition comprising an anthocyanin-negatively charged polysaccharide complex as an active ingredient for the prevention or treatment of gastritis or peptic ulcer.

It is another object of the present invention to provide a food composition comprising an anthocyanin-negatively charged polysaccharide complex as an active ingredient for the prevention or amelioration of gastritis or peptic ulcer.

It is another object of the present invention to provide a health functional food or a health supplement food comprising the food composition.

To achieve the above objects, the present invention provides a pharmaceutical composition comprising an anthocyanin-negatively charged polysaccharide complex as an active ingredient for the prevention or treatment of gastritis or peptic ulcer.

The present invention also provides a food composition comprising an anthocyanin-negatively charged polysaccharide complex as an active ingredient for the prevention or amelioration of gastritis or peptic ulcer.

In addition, the present invention provides a health functional food or a health supplement food comprising the food composition.

The present invention also provides a method for preventing or treating gastritis or peptic ulcer comprising a step of administering the pharmaceutical composition comprising an anthocyanin-anionic polysaccharide complex as an active ingredient for the prevention or treatment of gastritis or peptic ulcer to a mammal including humans in a therapeutically effective amount.

The present invention also provides a use of the pharmaceutical composition comprising an anthocyanin-anionic polysaccharide complex as an active ingredient for the prevention or treatment of gastritis or peptic ulcer for the manufacture of a preparation for gastritis or peptic ulcer.

In addition, the present invention provides a use of the pharmaceutical composition comprising an anthocyanin-anionic polysaccharide complex as an active ingredient for the prevention or treatment of gastritis or peptic ulcer for the treatment of gastritis or peptic ulcer.

Hereinafter, the present invention is described in detail.

A Pharmaceutical Composition Comprising an Anthocyanin-Negatively Charged Polysaccharide Complex as an Active Ingredient for the Prevention or Treatment of Gastritis or Peptic Ulcer The present invention provides a pharmaceutical composition comprising an anthocyanin-negatively charged polysaccharide complex as an active ingredient for the prevention or treatment of gastritis or peptic ulcer.

Aronia (Aronia melanocarpa) is a kind of berry belonging to Rosaceae, and is native to Northeast America and Eastern Europe. Aronia, which has a dark red color, has been widely cultivated around the world in recent years, and as a garden species, aronia is cultivated as a crossbreeding between two varieties. In particular, aronia is known to belong to the group with the highest anthocyanin among plants in nature. Aronia is known to contain many kinds of anthocyanin such as Cyanidin-3-galactoside, Cyanidin-3-glucoside, Cyanidin-3-arabinoside and Delphinidin-3-glucoside, and it is also known to contain a large amount of phenol. This aronia has been confirmed to have excellent antioxidant, anti-inflammatory and immune enhancement effects through research, and many studies have been conducted on the efficacy of aronia related to diabetes and various cardiovascular diseases and cosmetics.

In the present invention, the 'anthocyanin' is a water-soluble pigment glycoside present in a plant, and refers to a natural plant pigment that exhibits colors such as purple, red, and blue depending on the acid concentration of the cell fluid, the chemical structure of the pigment compound, and the binding state with various metal ions. Recently, it is known that anthocyanin has various physiological activities, and for example, anti-aging activity, antibacterial activity, mutagenic inhibitory activity, cholesterol lowering activity, visual acuity improvement effect, blood vessel protection function, and anti-ulcer function have been identified.

In the present invention, the said anthocyanin may be isolated from a plant. The plant can include any plant that produces anthocyanin, and can be, for example, black rice, black bean, black currant, chokeberry, black chokeberry, cranberry, aronia, mulberry, cherry, raspberry, blueberry, blackberry, eggplant, acai, wild grape or grape, preferably aronia.

In the present invention, the said anthocyanin can be at least one selected from the group consisting of peonidin, cyanidin 3-arabinoside, cyanidin-3-(xylosylglucose)-5-galactose, cyanidien-3-xyloside, cyanidin3-glucoside, cyanidin 3-galactoside, cyanidin-3-(coumaroyl-xylosylglucose)-5-galactose, delphinidin 3-glucoside, delphinidin 3-rutinoside, peonidin 3-arabinoside, peonidin 3-galactoside, petunidin 3-glucoside, cyanidin, delphinidin, malvidin, pelargonidin, peonidin, cyanidin 3,5-diglucoside, cyanidin 3-rutinoside, pelargonidin 3-glucoside, peonidin 3-glucoside, malvidin 3-glucoside and malvidin 3,5-diglucoside. Preferably, it can be cyanidin-3-galactoside, cyaniding-3-glucoside, cyaniding-3-arabinoside, or cyaniding-3-xyloside.

In the present invention, the said negatively charged polysaccharide is not particularly limited as long as it has biocompatibility, and may include one or more negatively charged functional groups. The term 'polysaccharide' refers to a polymer of two or more monosaccharide molecules, wherein the monosaccharides can be the same or different. The polysaccharide of the present invention can or cannot be cross-linked.

The complex of the present invention can be formed by using negatively charged polysaccharide itself, or by introducing a chemical modification to a general polysaccharide containing no or a small amount of negatively charged functional groups to impart negatively charged functional groups. The negatively charged functional group may be, for example, one or two or more carboxyl groups or sulfate groups.

In a specific example, the said negatively charged polysaccharide can be selected from the group consisting of hyaluronic acid, o-sulfated hyaluronic acid (o-sulfated HA), dextran sulfate, chondroitin sulfate, dermatan sulfate, keratin sulfate, heparin, heparin sulfate, alginic acid, fucoidan, carrageenan, mixtures thereof, and complexes thereof, preferably alginic acid, but not always limited thereto.

The negatively charged polysaccharide is a material frequently used in foods and beverages, and is not only harmless to the human body, but also has a strong negative charge in a neutral solution, so that it can form a complex by effectively ionic bonding with positively charged anthocyanin.

The polysaccharide is not particularly limited, but may have a weight average molecular weight in the range of about 1000 to 1,000,000, preferably in the range of about 10000 to 300,000, and more preferably in the range of 20,000 to 50,000.

In the negatively charged polysaccharide of the present invention, the encapsulation rate of anthocyanin can be controlled by adjusting the ionic bonding ratio with anthocyanin using the type and number of negative charges of the polysaccharide. Accordingly, as long as it is a polysaccharide having a negative charge, one or more types of polysaccharides having various molecular weights can be used depending on the purpose. The weight ratio of anthocyanin and negatively charged polysaccharide in the complex can be 1:1 to 100, preferably 1:5 to 100, more preferably 1:5 to 80, and most preferably 1:10 to 50. Within the above range, the complex formed from the polysaccharide of the present invention may exhibit advantageous effects in terms of enhancing the stability and physiological activity of anthocyanin.

Anthocyanin has high stability at low pH, and is known to have the highest stability and highest antioxidant activity, especially at pH 3 or lower. In addition, since anthocyanin has a positive charge at pH 3 or less, it can be structurally stable by forming a complex through an ionic bond with a negatively charged polysaccharide having biocompatibility. Because the anthocyanin-negatively charged polysaccharide nanocomplex has excellent oxidative stability and storage stability, it is possible to improve processing conditions and storage properties when it is applied to pharmaceuticals or food. In addition, when the complex is used, in vivo absorption can be increased due to the stability enhancement, which may be very useful for drug development.

In the present invention, the complex may have a size in the range of 10 nm to 1000 μm by forming a complex of anthocyanin and negatively charged polysaccharide, and anthocyanin may be encapsulated by polysaccharides, but not always limited thereto. The anthocyanin-negatively charged polysaccharide complex according to the present invention can be a suspension or powder depending on the purpose or field of use.

In some cases, the anthocyanin-negatively charged polysaccharide complex can further include a biocompatible or biodegradable carrier. In this case, the anthocyanin-negatively charged polysaccharide complex is in or a part of the carrier, and the carrier can be a liposome, a micelle, or a polymerized vesicle.

In the most preferred form of the complex of the present invention, the negatively charged polysaccharide can be alginic acid, and the weight average molecular weight is in the range of 20,000 to 50,000.

In the present invention, the method for preparing the anthocyanin-negatively charged polysaccharide complex is not particularly limited, but the complex can preferably be prepared by a method comprising the following steps:

(i) forming an anthocyanin-anionic polysaccharide complex in acidic environment; and/or (ii) recovering the complex formed above.

In another embodiment, the method for preparing the anthocyanin-negatively charged polysaccharide complex can include the following step:

(iii) forming an anthocyanin-negatively charged polysaccharide complex in neutral or acidic environment.

When forming the anthocyanin-negatively charged polysaccharide complex, the solvent is not particularly limited, but edible ones are better. After preparing negatively charged polysaccharide and anthocyanin in appropriate proportions, stir the two solutions evenly and wait until the complex is completely formed.

The complex formed by the method of (i) above may maintain an acidic environment as it is in the case of an oral preparation depending on the dosage form, but when used as an injection, it is preferable to neutralize the pH by the method of (ii).

The difference between using the methods of (i) and (iii) is different depending on what kind of functional group the polysaccharide forming the complex has. For example, both methods of (i) and (iii) can be used for the polysaccharides having sulfate group because of their low pKa value, but for the polysaccharides having carboxyl group, it is suitable to use the method of (iii). Although the method of (i) can be used for the polysaccharides having carboxyl group, the complex must be stably formed with anthocyanin only through the process of (ii).

In the present invention, the said gastritis includes both acute gastritis and chronic gastritis, and the cause of the occurrence is not particularly limited, but it can be caused by Helicobacter pylori infection, NSAIDS (non-steroidal anti-inflammatory drugs) intake, alcohol intake, stress, etc., preferably it can be caused by NSAIDS intake or alcohol intake, and more preferably it can be caused by alcohol intake.

On the other hand, it will be apparent to those skilled in the art that the gastritis in the present invention can also include esophagitis.

In the present invention, the peptic ulcer can be selected from the group consisting of duodenal ulcer, gastric ulcer, small intestine ulcer and large intestine ulcer, and preferably can be duodenal ulcer or gastric ulcer.

Meanwhile, in the present specification, 'comprising as an active ingredient' means including an amount sufficient to achieve the efficacy or activity of the anthocyanin-negatively charged polysaccharide complex. In one embodiment of the present invention, the anthocyanin-negatively charged polysaccharide complex in the composition of the present invention is, for example, 0.001 mg/kg or more, preferably 0.1 mg/kg or more, more preferably 10 mg/kg or more, even more preferably 100 mg/kg or more, more preferably 250 mg/kg or more, and most preferably 0.1 g/kg or more. Since the anthocyanin-negatively charged polysaccharide complex is a natural product and has no side effects even when administered in excess, the upper limit of the quantity of the anthocyanin-negatively charged polysaccharide complex contained in the composition of the present invention can be selected within an appropriate range by those skilled in the art.

The pharmaceutical composition of the present invention can be prepared using a pharmaceutically suitable and physiologically acceptable adjuvant in addition to the active ingredient. As the adjuvant, an excipient, a disintegrant, a sweetener, a binder, a coating agent, an expanding agent, a lubricant, a slip modifier, or a flavoring agent can be used.

The pharmaceutical composition can be preferably formulated as a pharmaceutical composition by including one or more pharmaceutically acceptable carriers in addition to the active ingredients described above for administration.

The pharmaceutically acceptable carrier is the one that is generally used in the art, which is exemplified by lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate and mineral oil, but not always limited thereto. In addition, the pharmaceutical composition of the present invention can additionally include diluents or excipients such as fillers, extenders, binders, wetting agents, disintegrants and surfactants, and other pharmaceutically acceptable additives.

Formulations of the pharmaceutical composition can be granules, powders, tablets, coated tablets, capsules, suppositories, solutions, syrups, juices, suspensions, emulsions, drops or injectable solutions. For example, for formulation in the form of tablets or capsules, the active ingredient can be combined with an orally, non-toxic, pharmaceutically acceptable inert carrier such as ethanol, glycerol, water, and the like. In addition, if desired or necessary, suitable binders, lubricants, disintegrants and color-developing agents can also be included in the mixture. The suitable binder includes starch, gelatin, natural sugars such as glucose or beta-lactose, corn sweeteners, natural and synthetic gums such as acacia, tracacanth or sodium oleate, sodium stearate, magnesium stearate, sodium benzoate, sodium acetate, sodium chloride, and the like, but not always limited thereto. The disintegrant includes starch, methyl cellulose, agar, bentonite, xanthan gum, and the like, but not always limited thereto.

In the composition formulated as a liquid solution, the pharmaceutically acceptable carrier is sterile and biocompatible, and can be used by mixing saline, sterile water, Ringer's solution, buffered saline, albumin injection, dextrose solution, maltodextrin solution, glycerol, ethanol, and one or more of these components. If necessary, other conventional additives such as antioxidants, buffers, and bacteriostats can be added. In addition, the composition of the present invention can be formulated in different forms including aqueous solutions, suspensions and emulsions for injection, pills, capsules, granules or tablets by mixing with diluents, dispersing agents, surfactants, binders and lubricants.

The composition can further be prepared in suitable forms according to ingredients by following the method represented in Remington's Pharmaceutical Science, Mack Publishing Company, Easton PA.

The pharmaceutical composition of the present invention can be administered orally or parenterally, and in the case of parenteral administration, it can be administered by intravenous injection, subcutaneous injection, intramuscular injection, intraperitoneal injection, transdermal administration, etc., but oral administration is preferred.

In the present invention, the term 'oral administration' is a method of injecting a drug for alleviating pathological symptoms through the mouth. In the present invention, the term 'parenteral administration' refers to a method of subcutaneous, intramuscular, intravenous, or intraperitoneal administration using a tube, except for oral administration.

The pharmaceutical composition of the present invention can be orally administered to mammals such as rats, mice, livestock, and humans.

For formulations for parenteral administration, sterile aqueous solutions, liquids, non-aqueous solutions, suspensions, emulsions, eye drops, eye ointments, syrups, suppositories, external preparations such as aerosols, and sterilized injections can be prepared by the conventional method, and preferably skin external pharmaceutical compositions such as creams, gels, patches, sprays, ointments, plasters, lotions, liniments, pastes or cataplasms can be prepared, but not always limited thereto. Compositions for topical administration can be anhydrous or aqueous, depending on the clinical prescription. Non-aqueous solutions and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerogelatin, etc.

A suitable dosage of the pharmaceutical composition of the present invention varies depending on factors such as formulation method, administration method, age, weight, gender, pathological condition, food, administration time, administration route, excretion rate and reaction sensitivity of a patient. An effective dosage for the desired treatment or prophylaxis can be easily determined and prescribed by an ordinary skilled doctor. According to a preferred embodiment of the present invention, the daily dose of the pharmaceutical composition of the present invention is 0.001-10 g/kg.

The pharmaceutical composition of the present invention can be formulated by the method that can be performed by those in the art by using a pharmaceutically acceptable carrier and/or excipient in the form of unit dose or in multi-dose container. The formulation can be in the form of solution, suspension or emulsion in oil or water-soluble medium, extract, powder, granule, tablet or capsule. At this time, a dispersing agent or a stabilizer can be additionally included.

A Food Composition Comprising an Anthocyanin-Negatively Charged Polysaccharide Complex as an Active Ingredient for the Prevention or Amelioration of Gastritis or Peptic Ulcer The present invention also provides a food composition comprising an anthocyanin-negatively charged polysaccharide complex as an active ingredient for the prevention or amelioration of gastritis or peptic ulcer.

In the present invention, the term 'amelioration' refers to any action that improves the bad state of cachexia by administering or ingesting the composition of the present invention to a subject.

The food composition according to the present invention can be formulated in the same manner as the pharmaceutical composition and used as a functional food or added to various foods. For example, the composition of the present invention can be added to beverages, alcoholic beverages, snacks, diet bars, dairy products, meats, chocolates, pizza, ramyuns, other noodles, gums, ice creams, hangover remedies (drinks, low-viscosity gels, pills, tablets, capsules, etc.), vitamin complexes, health supplements, etc.

The food composition of the present invention can include not only the anthocyanin-negatively charged polysaccharide complex as an active ingredient, but also ingredients commonly added during food production, for example, proteins, carbohydrates, fats, nutrients, seasonings and flavoring agents. The carbohydrates described above can be one of monosaccharides such as glucose and fructose; disaccharides such as maltose, sucrose and oligosaccharides; polysaccharides such as dextrin and cyclodextrin, and glucose alcohols such as xilytole, sorbitol and erythritol. Besides, natural sweetening agents (thaumatin, stevia extract, for example rebaudioside A, glycyrrhizin, etc.) and synthetic sweetening agents (saccharin, aspartame, etc.) can be included as a sweetening agent. For example, when the food composition of the present invention is prepared as a drink or beverage, citric acid, high fructose corn syrup, sugar, glucose, acetic acid, malic acid, fruit juice, and various plant extracts can be additionally included in addition to the anthocyanin-negatively charged polysaccharide complex of the present invention.

The present invention provides a health functional food or a health supplement food comprising the food composition containing an anthocyanin-negatively charged polysaccharide complex as an active ingredient. The said health functional food or health supplement food refers to a food manufactured and processed using raw materials or ingredients useful for the human body according to the health functional foods act. The term 'functional' refers to ingestion for the purpose of obtaining useful effects for health purposes such as regulating nutrients for the structure and function of the human body or physiological effects. In the present invention, the health functional food is a food prepared by adding the anthocyanin-negatively charged polysaccharide complex to food materials such as beverages, teas, spices, gums, snacks, or the like, or prepared by the anthocyanin-anionic polysaccharide complex in capsules, powders, suspensions, and the like. In case of ingestion of the above food, it brings specific health effects, and unlike general medicines, there are no side effects that may occur when taking the medicine for a long time by using food as a raw material. The health functional food or health supplement food of the present invention obtained in this way is very useful because it can be consumed on a daily basis. The amount of the anthocyanin-negatively charged polysaccharide complex added in such health functional food or health supplement food varies depending on the type of the target health functional food and cannot be uniformly defined, but can be added within a range that does not impair the original taste of the food. Specifically, the amount of the complex added is usually in the range of 0.01 to 50 weight %, and preferably 0.1 to 20 weight % based on the target food. In addition, in the case of the health functional food or health supplement food in the form of pills, granules, tablets or capsules, it is usually added in an amount of 0.1 to 100 weight %, and preferably 0.5 to 80 weight %. In one embodiment of the present invention, the health functional food or health supplement food of the present invention can be in the form of pills, tablets, capsules or beverages.

The food composition of the present invention can include conventional food additives. Whether or not it is suitable as a 'food additive' is judged according to the specifications and standards for the relevant items in accordance with the general rules and general test methods of the Food Additives Code approved by the Ministry of Food and Drug Safety, unless otherwise specified.

The items listed in the 'Food Additives Code' include, for example, chemical compounds such as ketones, glycine, potassium citrate, nicotinic acid and cinnamic acid; natural additives such as persimmon pigment, licorice extract, crystalline cellulose, kaoliang color and guar gum; and mixed preparations such as sodium L-glutamate preparations, alkali additives for noodles, preservatives and tar color formulations.

In addition, the food composition of the present invention can be manufactured and processed in the form of tablets, capsules, powders, granules, liquids, and pills for the purpose of preventing and/or ameliorating gastritis or peptic ulcer.

For example, the health functional food in the form of tablets can be prepared by granulating a mixture of a pharmaceutical composition comprising the anthocyanin-negatively charged polysaccharide complex according to the present invention as an active ingredient, an excipient, a binder, a disintegrant, and other additive in a conventional manner, followed by compression molding by adding a lubricant. Alternatively, the mixture can be directly compression molded. In addition, the health functional food in the form of tablets can contain a flavor enhancer, etc., and can be coated with a suitable coating agent if necessary.

Among the health functional food in the form of capsules, hard capsules can be prepared by filling conventional hard capsules with a mixture of a pharmaceutical composition comprising the anthocyanin-negatively charged polysaccharide complex according to the present invention as an active ingredient and an excipient, the granules thereof or the coated granules thereof. Soft capsules can be prepared by filling capsule base such as gelatin with a mixture of the food composition according to the present invention and additives such as excipients. The soft capsules can contain a plasticizer such as glycerin or sorbitol, a colorant, a preservative, and the like, if necessary.

The health functional food in the form of pills can be prepared by molding a mixture of a pharmaceutical composition comprising the anthocyanin-negatively charged polysaccharide complex according to the present invention as an active ingredient, an excipient, a binder, a disintegrant, and the like using an appropriate method. If necessary, the pills can be coated with sucrose or other suitable coating agents, or can be coated with starch, talc or a suitable material.

The health functional food in the form of granules can be prepared by granulating a mixture of a pharmaceutical composition comprising the anthocyanin-negatively charged polysaccharide complex according to the present invention as an active ingredient, an excipient, a binder, a disintegrant, and the like using an appropriate method, and may contain flavoring agents, flavor enhancers, etc. as necessary. When a particle size test was performed using No. 12 (1680 μm), 14 (1410 μm) and 45 (350 μm) sieves, the total amount of the health functional food granules passed through No. 12 sieve, 5.0% or less of the total amount of the health functional food granules remained on No. 14 sieve, and 15.0% or less of the total amount of the health functional food granules passed through No. 45 sieve.

The term definitions for the excipients, binders, disintegrants, lubricants, flavor enhancers, flavoring agents, and the like are described in documents known in the art and include those having the same or similar functions (The Korean Pharmacopoeia, Moonsung Publishing Co., Korean Association of Pharmacy Education, 5$^{th}$ edition, p33-48, 1989).

The food herein is not particularly limited, and in wide sense, almost every health functional food can be included.

A Method for Preventing or Treating Gastritis or Peptic Ulcer

The present invention provides a method for preventing or treating gastritis or peptic ulcer comprising a step of administering the pharmaceutical composition comprising an anthocyanin-anionic polysaccharide complex as an active ingredient for the prevention or treatment of gastritis or peptic ulcer to a mammal including humans in a therapeutically effective amount.

In this specification, the term 'therapeutically effective amount' is an amount effective for preventing or treating gastritis or peptic ulcer, for example, an amount of a pharmaceutical composition for preventing or treating gastritis or peptic ulcer comprising an anthocyanin-anionic polysaccharide complex as an active ingredient administered to a subject to be treated. The therapeutically effective amount includes an amount that prevents the occurrence or recurrence of gastritis or peptic ulcer, an amount that alleviates the symptoms, an amount that inhibits direct or indirect pathological consequences, an amount that prevents the metastasis, an amount that reduces the rate of progression, an amount that alleviates or temporarily ameliorates the state, and an amount of the pharmaceutical composition for preventing or treating gastritis or peptic ulcer comprising an anthocyanin-anionic polysaccharide complex as an active ingredient that improves the prognosis. That is, the therapeutically effective amount can be interpreted as encompassing all amounts that improve or cure the symptoms of gastritis or peptic ulcer by the pharmaceutical composition for preventing or treating gastritis or peptic ulcer comprising an anthocyanin-anionic polysaccharide complex as an active ingredient.

A method of preventing or treating gastritis or peptic ulcer includes not only controlling the disease itself before the onset of the symptoms, but also inhibiting or avoiding the symptoms by administering the pharmaceutical composition for preventing or treating gastritis or peptic ulcer comprising an anthocyanin-anionic polysaccharide complex as an active ingredient. In the management of a disease, the prophylactic or therapeutic dose of a particular active ingredient may vary depending on the nature and severity of the disease and the route by which the active ingredient is administered. The dose and frequency of dose may vary according to the age, weight and response of an individual patient. A suitable dosage regimen can be readily selected by one of ordinary skill in the art taking these factors into account. In addition, the prophylactic or therapeutic method of the present invention can further include administration of a therapeutically effective amount of an additional active agent useful for the prevention or treatment of gastritis or peptic ulcer together with the pharmaceutical composition for preventing or treating gastritis or peptic ulcer comprising an anthocyanin-anionic polysaccharide complex as an active ingredient. The additional active agent can exhibit a synergistic or additive effect with the pharmaceutical composition for preventing or treating gastritis or peptic ulcer comprising an anthocyanin-anionic polysaccharide complex as an active ingredient.

The mammals including humans include mammals such as humans, monkeys, cattle, horses, dogs, cats, rabbits, and rats.

A Use of the Pharmaceutical Composition for the Prevention or Treatment of Gastritis or Peptic Ulcer The present invention provides a use of the pharmaceutical composition comprising an anthocyanin-anionic polysaccharide complex as an active ingredient for the prevention or treatment of gastritis or peptic ulcer for the manufacture of a preparation for gastritis or peptic ulcer.

The present invention provides a use of the pharmaceutical composition comprising an anthocyanin-anionic polysaccharide complex as an active ingredient for the prevention or treatment of gastritis or peptic ulcer for the treatment of gastritis or peptic ulcer.

The pharmaceutical composition comprising an anthocyanin-anionic polysaccharide complex as an active ingredient for the prevention or treatment of gastritis or peptic ulcer of the present invention for the manufacture of a preparation for gastritis or peptic ulcer can be mixed with an acceptable carrier and the like, and can further include other agonists.

Those mentioned in the pharmaceutical composition, food composition, prophylactic or therapeutic method and use of the present invention are equally applied as long as they do not contradict each other.

Advantageous Effect

The composition comprising an anthocyanin-negatively charged polysaccharide complex as an active ingredient provided by the present invention exhibits a significantly excellent effect of relieving lesions of gastritis or peptic ulcer, and thus can be very effectively used in the development of a composition for preventing, ameliorating, or treating gastritis or peptic ulcer.

DESCRIPTION OF THE PREFERRED EMBODIMENTS

Hereinafter, the present invention will be described in detail by the following examples. However, the following examples are only for illustrating the present invention, and the contents of the present invention are not limited thereto.

Example 1: Preparation of Anthocyanin-Negatively Charged Polysaccharide Complex Material Anthocyanin was obtained by crushing the raw fruit of aronia, adsorbing the juice to a polyphenol adsorption resin, eluting thereof with an ethyl alcohol aqueous solution, and pulverizing thereof. 20 mg of the anthocyanin powder prepared above was dissolved in 5 mℓ of phosphate buffer (pH 3, PB 3) at 40° C., and 200 mg of alginic acid (negatively charged polysaccharide) was dissolved in 10 mℓ of deionized water (D.I water) at room temperature. An anthocyanin-negatively charged polysaccharide complex (CANC) was prepared by adding the anthocyanin solution to the alginic acid solution (1:1, V/V), followed by stirring at room temperature for 48 hours.

Example 2: Effect of Anthocyanin-Negatively Charged Polysaccharide Complex in HCl-Ethanol-Induced Gastric Ischemic Inflammation Animal Model Sparague Dawley rats (male, 4 weeks old) were purchased and used for the test. The animals were sufficiently raised for more than 7 days. In the laboratory environment, lighting time was maintained for 12 hours, temperature was maintained at 22±2° C., and relative humidity was maintained at 50±5%.

1) The animals were fasted for 36 hours prior to oral administration of each test substance, and drinking water was allowed to take freely.
2) Experimental groups were divided into control group (Ctrl, water), omeprazole administration group (Omeprazole, Omp, 20 mpk (mg per kg weight)), alginic acid administration group (Alginate, 52.92 mpk), anthocyanin administration group (ABF, 1.27 mpk, 2.54 mpk and 5.08 mpk), and anthocyanin-alginic acid complex administration group (CANC, 1.27 mpk, 2.54 mpk and 5.08 mpk).
3) Test substances for each group were orally administered to each animal (2 μℓ/g, b.w.), and 0.3 M HCl/ethanol was orally administered (1 ml/rat) 1 hour after the drug administration. Drinking water was prohibited at the same time as drug administration was in progress.
4) After 1 hour of 0.3 M HCl/ethanol administration, the animals were killed with carbon dioxide and the stomach was extracted, fixed with 2% formalin solution for 10 minutes, and the damaged area in the stomach was photographed, and the length of the injury (mm) was measured using Image J software. The measured values were recorded as the ulcer index (mm).

Figure 1:
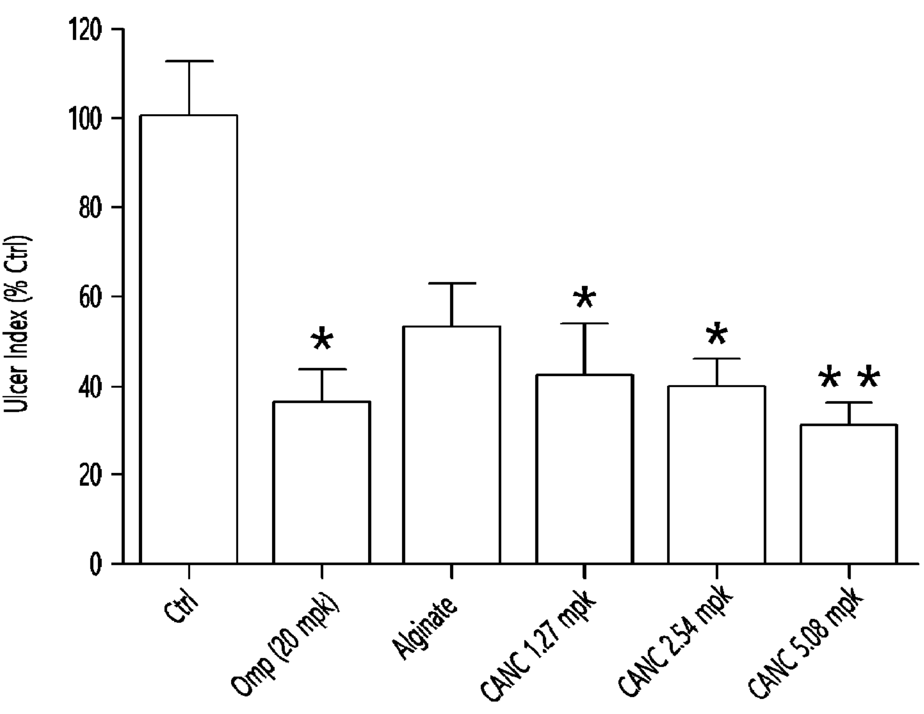
FIG. 1 is a graph showing the effect of the anthocyanin-negatively charged polysaccharide complex of the present invention. (Omp: omeprazole, CANC: anthocyanin-negatively charged polysaccharide complex, mpk: mg per kg weight)

The results are shown in FIG. 1. As shown in FIG. 1, the anthocyanin-alginic acid complex exhibited a significantly improved gastric inflammation amelioration effect compared to the group administered with each substance alone.

Figure 2:
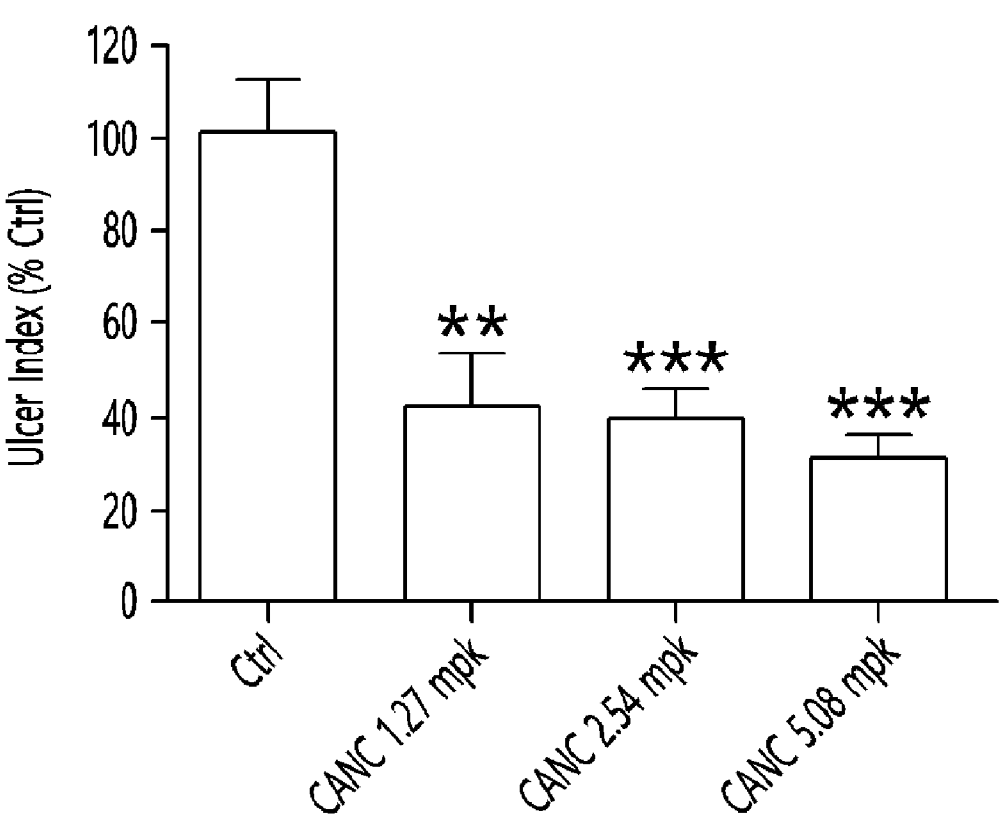
FIG. 2 is a graph showing the effect when the anthocyanin-negatively charged polysaccharide complex of the present invention treated alone. (CANC: anthocyanin-negatively charged polysaccharide complex, mpk: mg per kg weight)
Figure 3:
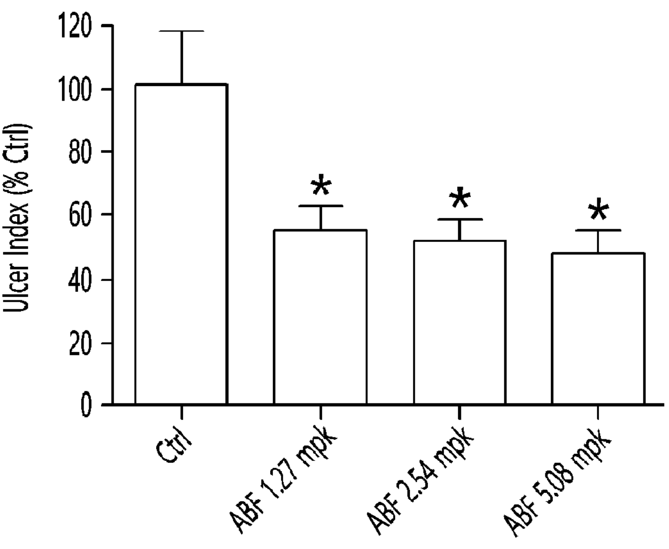
FIG. 3 is a graph showing the effect when the anthocyanin of the present invention treated alone. (ABF, adsorbed/eluted anthocyanin of the present invention, mpk: mg per kg weight)

As shown in FIGS. 2 and 3, the anthocyanin-alginic acid complex exhibited a statistically significant amelioration effect compared to the group administered with the anthocyanin (ABF) isolated in Example 1 alone (FIG. 2: anthocyanin-negatively charged polysaccharide complex administration group, FIG. 3: anthocyanin administration group). These results confirmed that a synergistic effect occurred by administering anthocyanin and negatively charged polysaccharides in combination in the form of a complex.

INDUSTRIAL APPLICABILITY

The composition comprising an anthocyanin-negatively charged polysaccharide complex as an active ingredient provided by the present invention exhibits a significantly excellent effect of relieving lesions of gastritis or peptic ulcer, and thus can be very effectively used in the development of a composition for preventing, ameliorating, or treating gastritis or peptic ulcer, so it has very high industrial applicability.

What is claimed is:

1. A method for preventing or treating gastritis or peptic ulcer, the method comprising administering to a mammal an ionically bonded anthocyanin-alginic acid complex in a therapeutically effective amount for preventing or treating gastritis or peptic ulcer, wherein the anthocyanin is obtained from a fruit of aronia and is a mixture comprising cyanidin-3-galactoside, cyanidin-3-glucoside, cyanidin-3-arabinoside and delphinidin-3-glucoside, and wherein the weight ratio of anthocyanin and alginic acid in the complex is 1:10 to 50.

2. A method for treating gastritis or peptic ulcer, the method comprising administering to a mammal having gastritis or peptic ulcer an ionically bonded anthocyanin-alginic acid complex in a therapeutically effective amount to treat the gastritis or peptic ulcer, wherein the anthocyanin is obtained from a fruit of aronia and is a mixture comprising cyanidin-3-galactoside, cyanidin-3-glucoside, cyanidin-3-arabinoside and delphinidin-3-glucoside, and wherein the weight ratio of anthocyanin and alginic acid in the complex is 1:10 to 50.

3. The method of claim 2, wherein the anthocyanin further comprises at least one selected from the group consisting of peonidin, cyanidin-3-(xylosylglucose)-5-ga lactose, cyanidin-3-xyloside, cyanidin-3-(coumaroyl-xylosylglucose)-5-galactose, delphinidin 3-rutinoside, peonidin 3-arabinoside, peonidin 3-galactoside, petunidin 3-glucoside, cyanidin, delphinidin, malvidin, pelargonidin, cyanidin 3,5-diglucoside, cyanidin 3-rutinoside, pelargonidin 3-glucoside, peonidin 3-glucoside, malvidin 3-glucoside, and malvidin 3,5-diglucoside.

4. The method of claim 2, wherein the peptic ulcer is selected from the group consisting of duodenal ulcer, gastric ulcer, small intestine ulcer and large intestine ulcer.

5. The method of claim 2, wherein the gastritis or peptic ulcer is alcoholic gastritis or alcoholic peptic ulcer.

* * * * *